United States Patent
Kronemeijer et al.

(10) Patent No.: US 6,621,265 B2
(45) Date of Patent: Sep. 16, 2003

(54) MEASURING A MATERIAL PROPERTY OF AN ELECTRICALLY CONDUCTIVE OBJECT

(75) Inventors: Dirk Arie Kronemeijer, Amsterdam (NL); Petrus Johannes Van De Loo, Amsterdam (NL); Mark Theodoor Looijer, Amsterdam (NL); Ricky Eduardo Ricardo Meyer, Amsterdam (NL)

(73) Assignee: Shell Oil Company, Houston, TX (US)

(*) Notice: Subject to any disclaimer, the term of this patent is extended or adjusted under 35 U.S.C. 154(b) by 0 days.

(21) Appl. No.: 10/028,843

(22) Filed: Dec. 20, 2001

(65) Prior Publication Data

US 2002/0149361 A1 Oct. 17, 2002

(30) Foreign Application Priority Data

Dec. 12, 2000 (EP) .............................. 00311519

(51) Int. Cl.[7] .................. G01R 33/12; G01N 27/72
(52) U.S. Cl. ...................... 324/239; 324/240
(58) Field of Search ..................... 324/239, 240, 324/229, 329, 207.17, 234, 238

(56) References Cited

U.S. PATENT DOCUMENTS 4,841,244 A 6/1989 Chambers
5,059,902 A 10/1991 Linder

FOREIGN PATENT DOCUMENTS

WO 98/02714 1/1998

OTHER PUBLICATIONS

International Search Report, dated Sep. 11, 2002.

Primary Examiner—Walter E. Snow

(57) ABSTRACT

The present invention relates to a device for measuring the value of a parameter relating to an electrically conductive object. Such a parameter can be the electric conductivity or the degree in which the material has changed under the influence of external conditions. Alternatively the parameter is the quality of a weld or the thickness of the object.

2 Claims, 1 Drawing Sheet

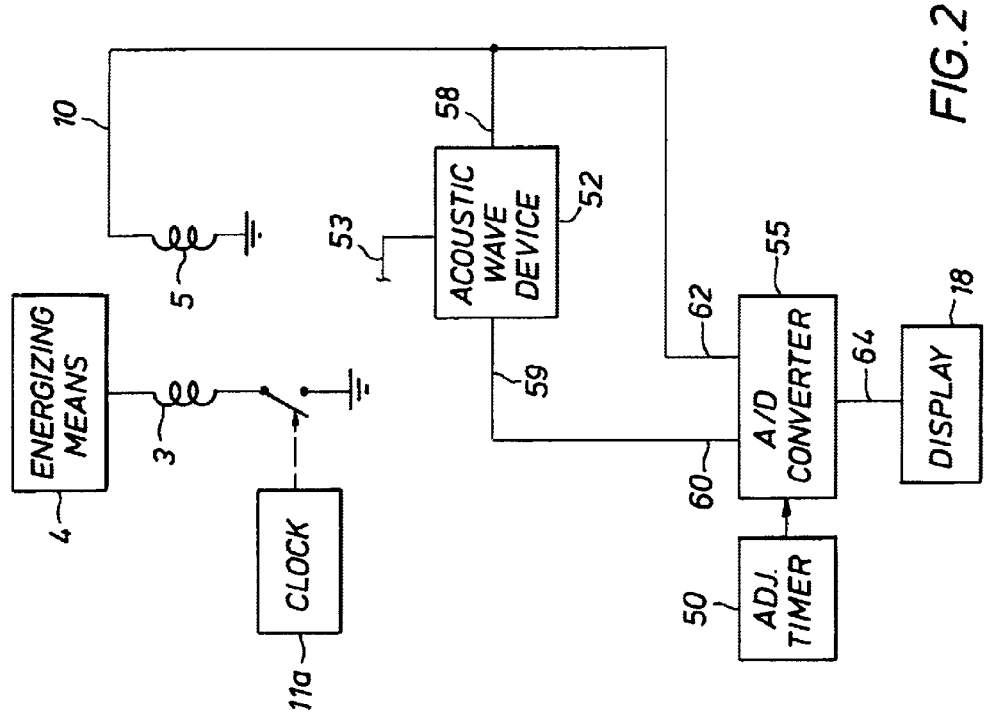
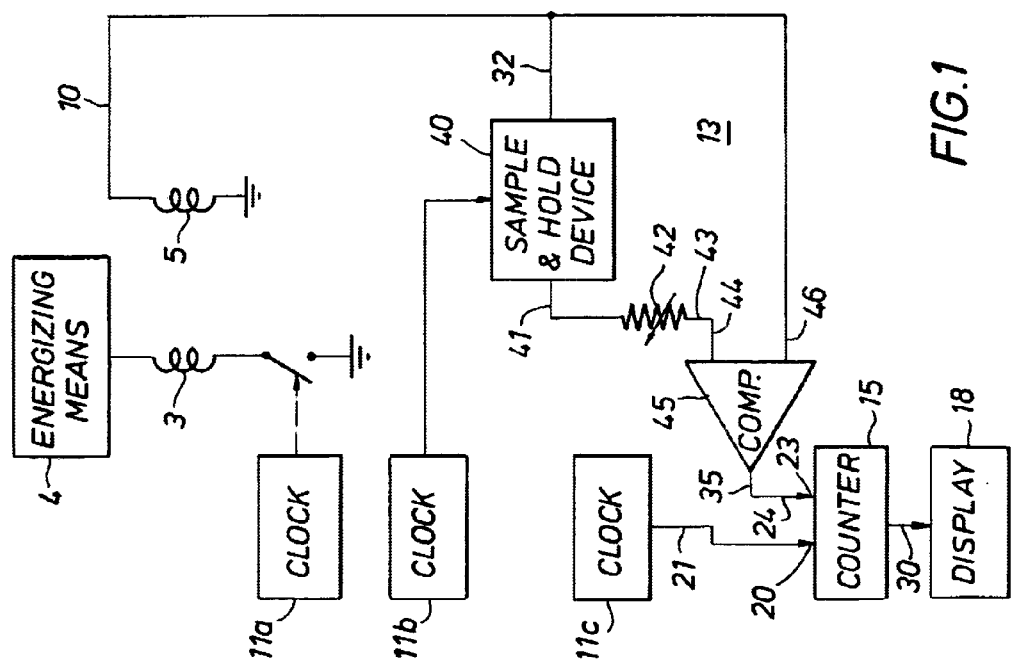
FIG. 2
FIG. 1

MEASURING A MATERIAL PROPERTY OF AN ELECTRICALLY CONDUCTIVE OBJECT

FIELD OF THE INVENTION

The present invention relates to a device for measuring the value of a parameter relating to an electrically conductive object. Such a parameter can be the electric conductivity or the degree in which the material has changed under the influence of external conditions. Alternatively the parameter is the quality of a weld or the thickness of the object.

BACKGROUND OF THE INVENTION

International patent application No. 98/02 714, hereby incorporated by reference, relates to measuring the wall thickness of an electrically conductive object. During normal operation, a pulsed eddy current is induced in the object, the decay of the eddy current is determined and a signal is produced representing the decay. The wall thickness can be determined from the signal representing the decay of the eddy current. The wall thickness is determined from the length of a time interval in which the signal decays from a first value to a second, lower, value. Determining the wall thickness involves a numerical operation.

U.S. Pat. No. 5,059,902, hereby incorporated by reference, discloses a device for measuring the value of a parameter relating to an electrically conductive object using a signal induced by decaying eddy currents in the object. The device comprises a transmitter coil, means for energizing the transmitter coil, a receiver coil having an output, a master clock, and a signal analysis unit, wherein the master clock controls the predetermined time during which the transmitter coil is energized and a second adjustable timer that controls the predetermined time during which the voltage is measured.

It would be advantageous to provide an alternative to the device known from U.S. Pat. No. 5,059,902, wherein the parameters relating to the electrically conductive object are measured with the method disclosed in International patent application, No. 98/02 714, wherein the result can be displayed on a display pertaining to the device, without the need for a numerical analysis.

In addition, it would be advantageous to provide a device that is so flexible that it can be used for such different activities as measuring the degree in which the material has changed under the influence of external conditions, determining the quality of a weld or measuring the thickness of the object.

SUMMARY OF THE INVENTION

The invention relates to a device for measuring a material property of an electrically conductive object and displaying a reading indicative of the material property on a display, which device comprises a transmitter coil, means for energizing the transmitter coil, a receiver coil having an output, a master clock, and a signal analysis unit comprising a hold-and-comparator unit and a digital counter, wherein the master clock comprises a first adjustable timer that controls the predetermined time during which the transmitter coil is energized, a second adjustable timer that controls the moment at which an initial value of the receiver coil signal is measured and held by the hold-and-comparator unit, and a third adjustable timer that controls the moment at which the digital counter starts, wherein the digital counter has a first input for a start-counting signal, a second input for a stop-counting signal and an output connected to the display, and wherein the hold-and-comparator unit has an input that is connected to the output of the receiver coil and an output that is connected to the second input of the digital counter, which hold-and-comparator unit outputs during normal operation a stop-counting signal if the value of the receiver coil signal is less than a scaled initial value of the receiver coil signal.

BRIEF DESCRIPTION OF THE DRAWINGS

FIG. 1 shows schematically a first embodiment of the invention; and

FIG. 2 shows schematically a second embodiment of the invention.

DETAILED DESCRIPTION OF THE INVENTION

A device for measuring a material property of an electrically conductive object and displaying a reading indicative of the material property on a display according to the present invention comprises a transmitter coil, means for energizing the transmitter coil, a receiver coil having an output, a master clock, and a signal analysis unit comprising a hold-and-comparator unit and a digital counter, wherein the master clock comprises a first adjustable timer that controls the predetermined time during which the transmitter coil is energized, a second adjustable timer that controls the moment at which an initial value of the receiver coil signal is measured and held by the hold-and-comparator unit, and a third adjustable timer that controls the moment at which the digital counter starts, wherein the digital counter has a first input for a start-counting signal, a second input for a stop-counting signal and an output connected to the display, and wherein the hold-and-comparator unit has an input that is connected to the output of the receiver coil and an output that is connected to the second input of the digital counter, which hold-and-comparator unit outputs during normal operation a stop-counting signal if the value of the receiver coil signal is less than a scaled initial value of the receiver coil signal.

In an alternative embodiment, the device for measuring a material property of an electrically conductive object and displaying a reading indicative of the material property on a display according to the present invention comprises a transmitter coil, means for energizing the transmitter coil, a receiver coil having an output, a master clock, and a signal analysis unit comprising a delay line having an adjustable delay and an analog-to-digital converter, wherein the master clock comprises a first adjustable timer that controls the predetermined time during which the transmitter coil is energized, and a second adjustable timer to start the analog-to-digital converter, wherein the acoustic wave device has an input that is connected to the output of the receiver coil and an output for a delayed signal that is connected to a first input of the analog-to-digital converter, and wherein the analog-to-digital converter has a second input that is connected to the output of the receiver coil and an output that is connected to the display.

The invention will now be described by way of example in more detail with reference to the accompanying drawings.

Reference is now made to FIG. 1. The device for measuring a material property of an electrically conductive object according to the present invention comprises a transmitter coil 3, means 4 for energizing the transmitter coil 3, a receiver coil 5 having an output 10, a master clock 11a, 11b, 11c, a signal analysis unit comprising a hold-and-comparator unit 13 and a digital counter 15, and a display 18.

The master clock comprises a first adjustable timer 11a that controls the predetermined time during which the transmitter coil 3 is energized, a second adjustable timer 11b that controls the moment at which an initial value of the receiver coil signal 10 is measured and held by the hold-and-comparator unit 13, and a third adjustable timer 11c that controls the moment at which the digital counter 15 starts.

The digital counter 15 has a first input 20 for a start-counting signal 21, a second input 23 for a stop-counting signal 24 and an output 30 connected to the display 18.

The hold-and-comparator unit 13 has an input 32 that is connected to the output 10 of the receiver coil 5 and an output 35 that is connected to the second input 23 of the digital counter 15. The hold-and-comparator unit 13 outputs during normal operation a stop-counting signal if the value of the receiver coil signal 10 is less than a scaled initial value of the receiver coil signal 10. To this end the hold-and-comparator unit 13 comprises a sample-and-hold device 40, of which the input 32 is connected to the output 10 of the receiver coil 5. The sample-and hold device 40 measures the value of the signal from the receiver coil 5 at a moment determined by the second adjustable clock 11b and holds the initial value for as long as necessary. The output 41 of the sample-and-hold device 40 is connected to a variable resistor 42 to scale the initial value, if necessary. The output 43 of the variable resistor 42 is connected to a first input 44 of a comparator 45. The second input 46 of the comparator 45 is connected to the output 10 of the receiver coil 5.

During normal operation, the first adjustable timer is set to energize the transmitter coil 3 during a predetermined period, for example 0.3 microseconds. At the end of this period the transmitter coil 3 is abruptly de-energized. The second adjustable timer 11b is set to measure value of the signal from the receiver coil 5 at a predetermined moment after de-energizing the transmitter coil 3, for example after 300 microseconds. The variable resistor 42 is set to scale the output of the sample-and-hold device 40 to a predetermined value, for example 20% of the output value. And the third adjustable timer 11c is set to start the counter 15 at a predetermined moment after de-energizing the transmitter coil 3, for example after 400 microseconds. It will be understood that the latter moment is selected after the moment on which the value of the signal is measured.

Then the device according to the present invention is positioned near an electrically conducting object (not shown) that is to be inspected, so that the transmitter coil 3 and the receiver coil 5 are close to the near surface of the object, and the measurement is started.

Energizing the transmitter coil 3 during a predetermined period and abruptly de-energizing the transmitter coil 3 induces an eddy current in the object. The decay of the eddy current is detected by the receiver coil 5, and its output is a signal representing the decay of the eddy current.

The sample-and-hold device 40 measures the value of the signal at a moment that is determined by the second adjustable timer 11b and holds the measured value, and this initial value is scaled down by the variable resistor 42 to the predetermined value. This scaled-down initial value 43 is compared in comparator 45 to the value of the output 10 of the receiver coil 5.

The counter 15 starts counting at a moment after de-energizing the transmitter coil 3 determined by the third adjustable timer 11c. The hold-and-comparator unit 13 outputs a stop-counting signal if the value of the receiver coil signal 10 is less than the scaled initial value 43 of the receiver coil signal 10.

The output of the counter 15 is then displayed on the display 18.

In general, the device will first be activated near a part of the object that can serve as a reference, so that any subsequent readings on the display 18 from different parts of the object can be compared to the readings pertaining to the reference.

Because four parameters can be set, the duration of the pulse, the moment at which the output from the receiver coil 5 is sampled, the variable resistor 42 and the moment at which the counter 15 starts counting, this device is very flexible. Thus it can be used for a large number of different types of measurements.

In this embodiment of the invention the time elapsed before a scaled-down value of the signal from the receiver coil 5 is used to measure a parameter of the object.

Reference is now made to FIG. 2 showing schematically an alternative embodiment of the present invention. In this embodiment, the decay of the output signal between two predetermined times is used to measure a parameter of the object. Parts of the device that are similar to the device as discussed with reference to FIG. 1 have the reference numeral used in FIG. 1.

The device for measuring a material property of an electrically conductive object comprises the transmitter coil 3, means 4 for energizing the transmitter coil 3, the receiver coil 5 having an output 10, a master clock 11a, 50, a signal analysis unit comprising a delay line in the form of acoustic wave device 52 having an adjustable delay 53 and an analog-to-digital converter 55, and the display 18.

The master clock comprises the first adjustable timer 11a that controls the predetermined time during which the transmitter coil 3 is energized, and a second adjustable timer 50 to start the analog-to-digital converter 55.

The acoustic wave device 52 has an input 58 that is connected to the output 10 of the receiver coil 5 and an output 59 for a delayed signal that is connected to a first input 60 of the analog-to-digital converter 55.

The analog-to-digital converter 55 has a second input 62 that is connected to the output 10 of the receiver coil 5 and an output 64 that is connected to the display 18.

During normal operation, the first adjustable timer 11a is set to energize the transmitter coil 3 during a predetermined period, for example 0.3 microseconds. At the end of this period the transmitter coil 3 is abruptly de-energized. The adjustable delay 53 of the acoustic wave device 52 is set to measure the value of the signal from the receiver coil 5 at a predetermined moment after de-energizing the transmitter coil 3, for example after 300 microseconds. The second adjustable timer 50 is set to trigger the analog-to-digital converter 55 to determine the difference between its input signals at a predetermined moment after de-energizing the transmitter coil 3, for example after 400 microseconds. It will be understood that the latter moment is selected after the moment on which the value of the signal is measured.

Then, the device according to the present invention is positioned near an object (not shown) that is to be inspected, so that the transmitter coil 3 and the receiver coil 5 are close to the near surface of the object, and the measurement is started.

Energizing the transmitter coil 3 during a predetermined period and abruptly de-energizing the transmitter coil 3 induces an eddy current in the object. The decay of the eddy current is detected by the receiver coil 5, and its output is a signal representing the decay of the eddy current.

The acoustic wave device delays outputting the signal 10 for a period determined by the adjustable delay 53.

The analog-to-digital converter 55 measures the difference between the delayed output 59 and the output 10 at a moment determined by the second adjustable timer 50.

The output of the analog-to-digital converter 55 is then displayed on the display 18.

The device will first be activated near a part of the object that can serve as a reference, so that any subsequent readings on the display 18 from different parts of the object can be compared to the readings pertaining to the reference.

Because three parameters can be set, the duration of the pulse, the delay of the acoustic wave device, and the moment at which the difference between the value of the delayed signal and the signal is measured, this device is also very flexible. Thus it can be used for a large number of different types of measurements.

The delay line is a device that introduces a predetermined delay in the transmission of a signal. Instead of an acoustic wave device, any other known device can be used.

The present invention therefore provides simple devices for measuring the value of several parameters relating to an electrically conductive object, that is for different types of measurements. Examples of such parameters are the chromium content of stainless steel, the degree of carbonisation of steel, the present of a sigma phase in steel and the degree of creep in a metal. Other parameters that can be measured are lift-off and thickness.

We claim:

1. A device for measuring a material property of an electrically conductive object and displaying a reading indicative of the material property on a display, said device comprising:
   a transmitter coil;
   a means for energizing the transmitter coil;
   a receiver coil comprising an output;
   a master clock comprising:
      a first adjustable timer that controls a predetermined time during which the transmitter coil is energized;
      a second adjustable timer that controls when an initial value of the receiver coil output is measured and held by a hold-and-comparator unit; and,
      a third adjustable timer that controls the moment at which a digital counter starts; and,
   a signal analysis unit comprising:
      a hold-and-comparator unit comprising:
         an input that is connected to the output of the receiver coil;
         a digital counter comprising:
            a first input for a start-counting signal;
            a second input for a stop-counting signal; and,
            an output connected to a display; and,
         an output that is connected to the second input of the digital counter; and,
      wherein the hold-and-comparator unit outputs during normal operation a stop-counting signal if the value of the receiver coil signal is less than a scaled initial value of the receiver coil signal.

2. A device for measuring a material property of an electrically conductive object and displaying a reading indicative of the material property on a display comprising:
   a transmitter coil;
   a means for energizing the transmitter coil;
   a receiver coil comprising an output;
   a master clock comprising:
      a first adjustable timer that controls when the transmitter coil is energized; and,
      a second adjustable timer to start an analog-to-digital converter;
   a signal analysis unit comprising:
      a delay line comprising:
         an adjustable delay; and,
         an analog-to-digital converter started by the second adjustable timer comprising:
            a first input;
            a second input connected to the output of the receiver coil; and,
            an output connected to a display; and,
      an acoustic wave device comprising:
         an input connected to the output of the receiver coil; and,
         an output or a delayed signal that is connected to the first input of the analog-to-digital converter.

* * * * *